(12) United States Patent
Kania et al.

(10) Patent No.: US 7,555,866 B2
(45) Date of Patent: Jul. 7, 2009

(54) RENEWABLY BUOYANT, SELF-PROTECTIVE FLOATING HABITAT

(75) Inventors: Bruce G. Kania, Shepherd, MT (US); Frank M. Stewart, Bozeman, MT (US); Russell F. Smith, Livingston, MT (US); Thomas N. Coleman, Livingston, MT (US); Alfred Cunningham, Bozeman, MT (US)

(73) Assignee: Fountainhead, LLC, Shepherd, MT (US)

( * ) Notice: Subject to any disclaimer, the term of this patent is extended or adjusted under 35 U.S.C. 154(b) by 0 days.

(21) Appl. No.: 10/595,735

(22) PCT Filed: Dec. 9, 2004

(86) PCT No.: PCT/US2004/041223

§ 371 (c)(1),
(2), (4) Date: May 8, 2006

(87) PCT Pub. No.: WO2005/058025

PCT Pub. Date: Jun. 30, 2005

(65) Prior Publication Data

US 2007/0124995 A1 Jun. 7, 2007

Related U.S. Application Data

(60) Provisional application No. 60/529,060, filed on Dec. 12, 2003, provisional application No. 60/609,187, filed on Sep. 10, 2004.

(51) Int. Cl.
*A01G 31/00* (2006.01)

(52) U.S. Cl. .................. 47/59 R; 47/65.5; 119/221

(58) Field of Classification Search ........... 119/221, 119/222, 223, 239; 47/59 R, 63, 65, 65.5, 47/66.7
See application file for complete search history.

(56) References Cited

U.S. PATENT DOCUMENTS

| 3,927,491 A | 12/1975 | Farnsworth |
| 4,037,360 A | 7/1977 | Farnsworth |
| 4,086,161 A | 4/1978 | Burton |
| 4,487,588 A | 12/1984 | Lewis, III et al. |
| 4,488,508 A * | 12/1984 | Heideman .................. 119/215 |
| 4,536,988 A | 8/1985 | Hogen |

(Continued)

FOREIGN PATENT DOCUMENTS

GB  2313326 A  * 11/1997

(Continued)

*Primary Examiner*—T. Nguyen
(74) *Attorney, Agent, or Firm*—Antoinette M. Tease

(57) ABSTRACT

A floating habitat designed to be renewably buoyant, self-sustaining and optionally specialized for waterfowl nesting. The first embodiment comprises one or more flotation units and a source of compressed air that is connected to the flotation units. Each flotation unit comprises an individual supply hose, an inflatable bladder, a relief valve, a diffusing manifold, bottom mesh, top mesh, and buoyant growth medium. An alternative embodiment comprises a self compensating buoyancy system. In the waterfowl nesting embodiment, the floating habitat includes one or more waterfowl nesting structures and construction material selected to optimize the nesting habitat. The floating habitat can be comprised of scrap pieces or layers of polyester mesh material. The Boating habitats can be combined to provide safe habitat for juvenile waterfowl, encourage colony nesting, or allow a variety of waterfowl or shore bird species to enjoy suitable habitat on the same floating habitat.

5 Claims, 13 Drawing Sheets

U.S. PATENT DOCUMENTS

| | | |
|---|---|---|
| 5,106,504 A | 4/1992 | Murray |
| 5,143,020 A | 9/1992 | Patrick |
| 5,224,292 A | 7/1993 | Anton |
| 5,261,185 A | 11/1993 | Koide et al. |
| 5,312,601 A | 5/1994 | Patrick |
| 5,337,516 A | 8/1994 | Hondulas |
| 5,528,856 A | 6/1996 | Smith et al. |
| 5,766,474 A | 6/1998 | Smith et al. |
| 5,799,440 A | 9/1998 | Ishikawa et al. |
| 5,836,108 A | 11/1998 | Scheuer |
| 5,980,738 A | 11/1999 | Heitkamp et al. |
| 5,992,104 A * | 11/1999 | Hudak ................ 52/167.1 |
| 6,000,551 A * | 12/1999 | Kanel et al. ............ 209/164 |
| 6,014,838 A | 1/2000 | Asher |
| 6,086,755 A | 7/2000 | Tepper |
| 6,555,219 B2 | 4/2003 | Kosinski |
| 2003/0051398 A1 | 3/2003 | Kosinski |
| 2003/0208954 A1 | 11/2003 | Bulk |
| 2005/0183331 A1 | 8/2005 | Kania et al. |

FOREIGN PATENT DOCUMENTS

| | | | |
|---|---|---|---|
| JP | 10113686 A | * | 5/1998 |
| JP | 11164630 A | * | 6/1999 |
| JP | 2001276861 A | * | 10/2001 |
| JP | 2002000098 A | * | 1/2002 |

* cited by examiner

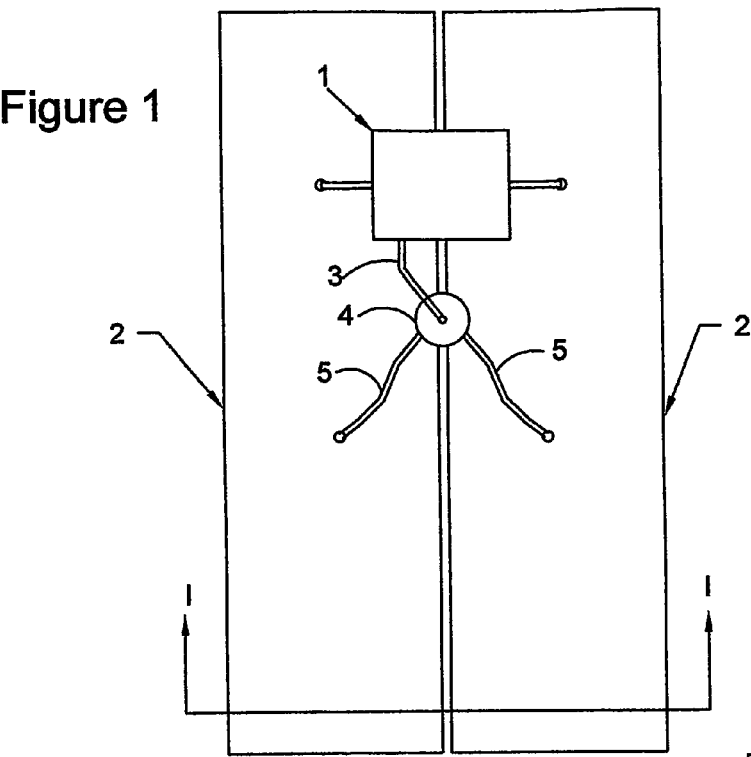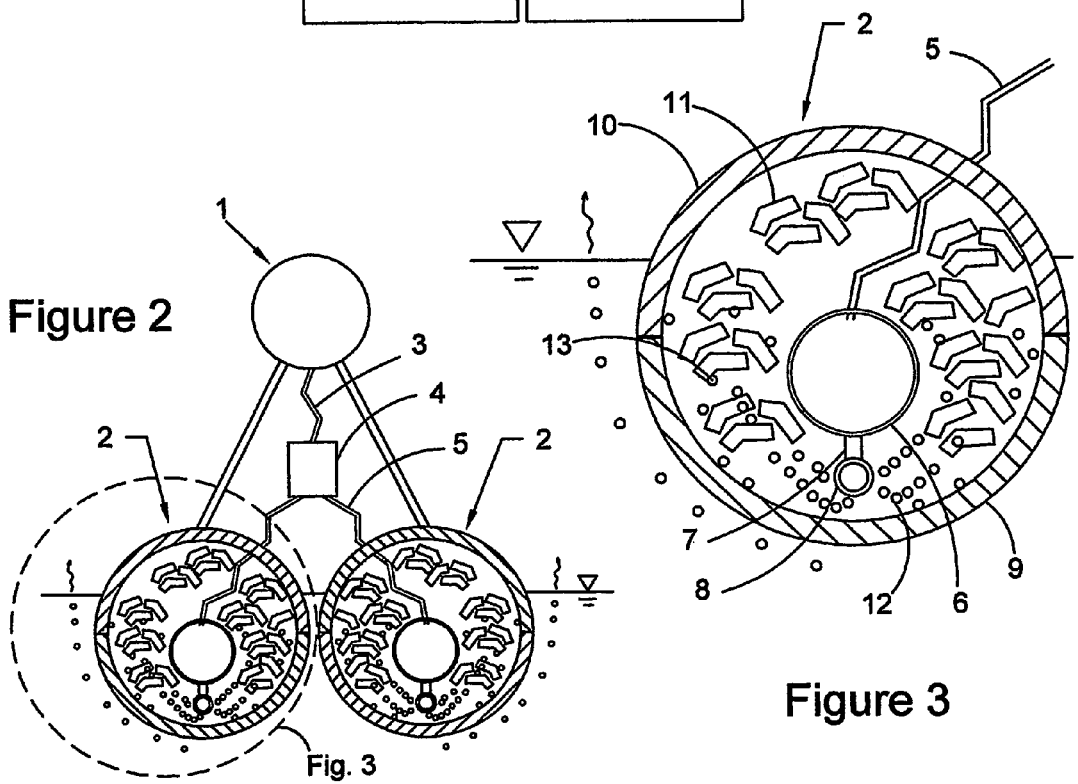

US 7,555,866 B2

RENEWABLY BUOYANT, SELF-PROTECTIVE FLOATING HABITAT

CROSS-REFERENCE TO RELATED APPLICATION

This application claims priority back to U.S. Patent Application No. 60/609,187 filed on Sep. 10, 2004 and U.S. Patent Application No. 60/529,060 filed on Dec. 12, 2003. The contents of these applications are hereby incorporated by reference into the present disclosure.

BACKGROUND OF THE INVENTION

1. Field of the Invention

The present invention relates to a floating habitat that has a dynamic ability to generate its own buoyancy, through the use of external power or by replicating the biotic activity that occurs on wild floating islands. The present invention encompasses a number of different embodiments directed toward providing waterfowl nesting habitat.

2. Description of the Related Art

Naturally occurring floating islands are a relatively unique phenomenon, but they do exist in several places in the world, including Australia, Bangladesh, Fiji, Germany, Hungary, India, Italy, Japan, Mexico, Poland, Turkey, Uganda and the United States. There has been much speculation and some research into how these floating islands form, and the answer appears to be specific to each location. Regardless of how they are formed, once present, floating islands provide a unique habitat for plants and some animal species, and they also play an important role in maintaining the health of the water body in which they are situated.

One of the objects of the present invention is to provide an artificial floating habitat that is similar to a naturally occurring floating island in terms of its aesthetic and functional value. It is a further object of the present invention to solve the problem of maintaining the buoyancy of an artificial floating island over time. Researchers have studied how naturally occurring floating islands maintain their buoyancy and have concluded that gas-producing microorganisms play a pivotal role. See Clark, 2000, infra; Hogg and Wein, 1988, infra. The present invention utilizes this research by incorporating microorganisms into the floating habitat structure as an option.

A naturally occurring floating island serves several purposes, not the least of which is the aesthetic value it adds to a body of water. It also serves as a habitat for various plant and animal species, and it helps purify the water by decreasing algae growth and slowing the natural process of eutrophication. In bodies of water such as ponds and lakes, algae growth and the natural process of eutrophication can lead to an increase in land mass and corresponding decrease in water volume, the killing of fish and other organisms, and the diminishment of aesthetic appearance.

Various floating mechanisms have been devised with the aim of mimicking some or all of the qualities of a naturally occurring floating island. Some examples of commercialized products along these lines are the artificial islands manufactured by Bestmann-Green of Germany, a "rafted floating ecology" produced by Ocean Arks International in Vermont, and a so-called "eco-island" made by MMG Civil Engineering Systems in the United Kingdom. Bestmann-Green has three floating island products—a laminar floating element of "girder" construction with a mat for rooting vegetation, a flexible vegetation unit made up of three triangular elements lying next to each other that are flexibly connected to form a single unit, and a modular system of metal frames with a net stretched within it and a planting mat connected to it. Ocean Arks describes its product as "assemblies of engineered ecologies on floating rafts." The primary function of their product is to purify wastewater, remove pollutants and digest sludge. The MMG eco-island is a framework of UV-protected PVC tubing with a rot-proof base. Buoyancy is created by watertight tubes that are sealed with specialty caps.

In addition to the products described above, there are a number of patents directed toward floating islands or other floating mechanisms designed to purify water, cultivate plants, dispense fertilizer, or counteract the effect of eutrophication. None of these inventions, however, anticipates the combination of features provided by the present invention.

U.S. Pat. No. 5,799,440 (Ishikawa et al, 1998) discloses a floating island comprising: (i) a planter with holes in it to allow the roots of the plants to grow into the water and to supply water to the soil in the planter; and (ii) an oxygen-generating agent container attached to the bottom of the planter. The planter is made of a foamed resin with a reinforcing film of polyurethane elastomer on the surface. The invention also includes: (i) a layer of porous material on the inner surface of the bottom of the planter that has an aerobic microorganism immobilized in it; and (ii) a plant cultivation bag to hold the soil. In the preferred embodiment, the oxygen-generating agent is calcium peroxide, and the soil in the planter is covered with a net or fabric that is permeable to water and air and is not harmful to the plants. In addition to generating oxygen, calcium peroxide also eliminates phosphorus, thereby restricting algae growth.

U.S. Pat. No. 4,086,161 (Burton, 1978) sets forth an ecological system and method for counteracting the effects of eutrophication in bodies of water such as marshlands, inland ponds and lakes. The system uses clusters of bark fibers positioned in the upper, relatively oxygen-rich zones of such bodies of water. These bark clusters attract and hold excessive nutrient deposition in the form of colloidal wastes and aquatic algae and also provide a safe habitat for algae predators and feeders.

U.S. Pat. No. 6,086,755 (Tepper, 2000) provides a floating hydroponic biofiltration device for use in a body of water containing plant-eating fish. The invention includes a float, a mesh and a matting. The float contains an aperture devoid of soil in which a terrestrial plant is inserted. The mesh is at a substantial depth below the float and serves to enable passage of oxygenated water to the plant roots while excluding large plant-eating fish. The mesh also serves as a substrate surface for the growth of nitrogen-converting bacteria, which convert the ammonia of fish waste to nitrates useful to plants. The matting anchors the plant roots and partially excludes plant-eating fish from a portion of the plant roots. In the preferred embodiment, the mesh and matting are formed of plastic.

U.S. Pat. No. 5,766,474 (Smith et al., 1998) and U.S. Pat. No. 5,528,856 (Smith et al., 1996) set forth a biomass impoundment management system that uses sunlight to purify water. The main purpose of this invention is to control impurities in water impoundments, such as ammonia, nitrogen, phosphorous and heavy metals. It is well known that nitrogen and phosphorous are primary food sources for various undesirable algae species, and ammonia and heavy metals are toxic to humans, fish and other organisms. This invention aims to purify water by allowing rooted bottom dwelling plants to grow and remain healthy on the bottom of a water impoundment while allowing rootless floating plants to grow and remain healthy above them. The non-rooted, floating plants are contained in a large surface area provided by elongated channels, which are oriented in a North-South direction to take full advantage of the sun. The elongated channels are designed to take advantage of wave activity to increase productivity.

U.S. Pat. No. 5,337,516 (Hondulas, 1994) sets forth an apparatus for treating waste water that includes a waste water basin and a number of wetland plants in floating containers. The idea underlying this invention is that the root systems of the wetland plants will treat the waste water. The extent of growth of the root systems is controlled by an adjustable platform associated with each floating container, so that the aerobic and anaerobic zones within the waste water basin are controlled and can be adjusted or varied as required. Similarly, U.S. Pat. No. 5,106,504 (Murray, 1992) covers an artificial water impoundment system designed to remove biologically fixable pollutants from urban or industrial waste water using aquatic plants to absorb pollutants.

U.S. Pat. No. 4,536,988 (Hogen, 1985) relates to a floating containment barrier grid structure for the containment of floating aquatic plants in a body of water. This invention is designed to facilitate the commercial cultivation and harvesting of aquatic plants. The grid structure consists of elongated flexible sheets that are interconnected at spaced intervals along their longitudinal axes to form a plurality of barrier sections in a web-like arrangement. Through the use of an anchoring means, the barrier grid is tensioned so that certain portions of the structure are submerged beneath the surface of the water by a device that harvests the floating aquatic plants.

U.S. Pat. No. 4,037,360 (Farnsworth, 1977) and U.S. Pat. No. 3,927,491 (Farnsworth, 1975) disclose a raft apparatus for growing plants by means of water culture or hydroponics. The raft floats on a nutrient solution, and buoyancy of the rafts is increased during plant growth by placing a small raft on a larger raft or on auxiliary buoyancy means. U.S. Pat. No. 5,261,185 (Kolde et al., 1973) also involves an apparatus floating on a nutrient solution. In this invention, rafts are floated in a water culture tank filled with nutrient solution, plant containers are inserted in vertically oriented channels in the raft, and the plants are cultivated by gradually moving the raft from one end of the water culture tank to another.

U.S. Pat. No. 4,487,588 (Lewis, III et al., 1984) addresses a submersible raft for the cultivation of plant life such as endangered sea grasses. The raft is manufactured from standard polyvinyl chloride tubing and fittings.

U.S. Pat. No. 6,014,838 (Asher, 2000) discloses a simple floatable unit for decorative vegetation. U.S. Pat. No. 5,836,108 (Scheuer, 1998) describes a floating planter box comprising a polyhedral planar base member of a synthetic foam resin less dense than water and an optional anchoring means.

U.S. Pat. No. 5,312,601 (Patrick, 1994) and U.S. Pat. No. 5,143,020 (Patrick, 1992) involve a simple apparatus for dispensing fertilizer in a pond. The invention consists of a flotation structure surrounded by a porous material such as a net sack and an opening in the flotation structure through which fertilizer is dumped. The fertilizer is dissolved by water flowing through the net sack at the bottom of the flotation structure.

BRIEF SUMMARY OF THE INVENTION

The present invention involves a floating habitat that is designed to be renewably buoyant and self-sustaining. The floating habitat comprises buoyant growth medium and optionally includes one or more inflatable bladders. The growth medium can be made of natural or synthetic material and can include plant growth enhancers. The inflatable bladders can be transparent or opaque and rigid or flexible. Gas-producing microorganisms can be added to the growth medium to provide additional buoyancy.

In the first embodiment, the floating habitat comprises one or more flotation units, a source of compressed air, and a means for connecting the source of compressed air to the flotation unit(s). Each flotation unit comprises an individual supply hose, an inflatable bladder, a relief valve, a diffusing manifold, bottom mesh, top mesh, and buoyant growth medium. The bottom and top mesh can be made of separate pieces of material or the same piece of material, and they can also be designed or modified to be resistant or unattractive to chewing animals. In the preferred embodiment, the mesh is sufficiently pliable, or the holes in the mesh are sufficiently large, to allow stems and roots to grow through it, and the mesh is also sufficiently rigid, or the holes in the mesh are small enough, to contain the buoyant growth medium. In an alternate embodiment, the diffusing manifold is positioned beneath the flotation unit by means of an extension tube. In yet another embodiment, the top and bottom mesh are replaced with top and bottom cover that is impermeable to water.

In another embodiment, the floating habitat is equipped with a self-compensating buoyancy system, which can take one of several forms. One possible embodiment of the self-compensating buoyancy system is a float valve system, in which buoyancy is regulated by a float valve with a ball float and a sealing face. When buoyancy needs to be increased, the ball float presses against the sealing face of the float valve, preventing air in the inflatable bladder from escaping into the atmosphere. When buoyancy needs to be decreased, the ball float is not in contact with the sealing face of the float valve, and air is allowed to escape from the inflatable bladder. At equilibrium, the ball float is lightly in contact with the sealing face of the float valve. Other embodiments of the self-compensating buoyancy system include a submersible, differential pressure gauge system, a conductivity switch, and an exhaust nozzle.

The floating habitat described above can also be specialized for waterfowl nesting. In this embodiment, the floating habitat includes one or more waterfowl nesting structures and, optionally, a predator control device. Live vegetation is selected based on the nesting preferences of a particular species of waterfowl, and the construction material and screen size of the top and bottom mesh are selected to optimize the nesting habitat. The present invention also includes a method of combining any number of the floating habitats described herein to provide safe habitat for juvenile waterfowl, to encourage colony nesting, or to allow for a variety of waterfowl or shore bird species to enjoy suitable habitat on the same floating habitat system. In an alternative embodiment, one or more waterfowl nesting structures are combined with an impermeable closed bag.

The present invention also includes a number of different embodiments of a waterfowl nesting structure that is made our of scrap pieces of polyester mesh material, expandable foam, and optionally, scrap pieces of closed cell foam. The sides of the habitat can be comprised of smooth, rigid plastic sheeting to prevent swimming animals from boarding the habitat. Camouflage material can be added to provide protection for a nesting area and/or nesting cavity. Jute or a similar natural-looking material can be added to the top of the structure to improve its appearance. The bottom of the habitat can be either penetrable or non-penetrable by plant roots, as desired.

BRIEF DESCRIPTION OF THE DRAWINGS

FIG. 1 is a top view of a first embodiment of the present invention.

FIG. 2 is a section view taken at I-I of FIG. 1.

FIG. 3 is a partial section view of a first embodiment of the present invention.

REFERENCE NUMBERS

Figure 4:
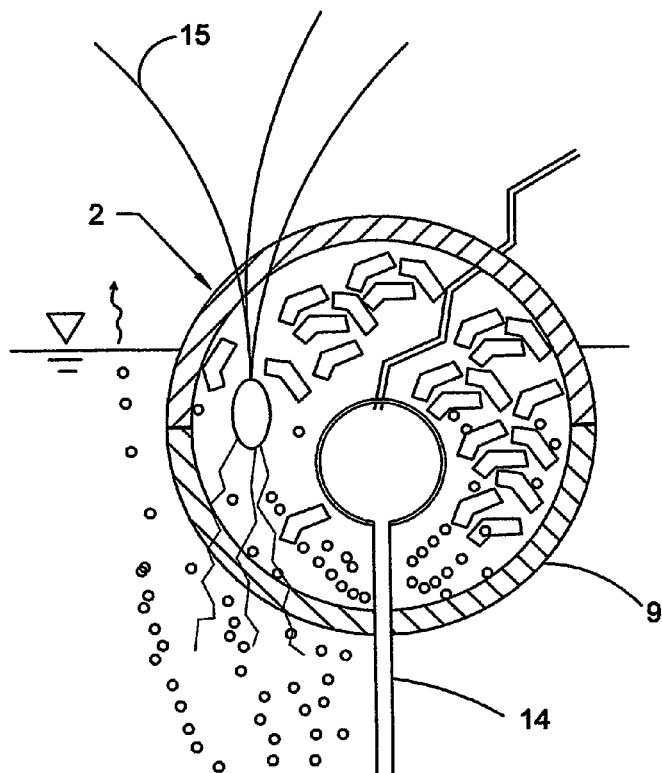
FIG. 4 is a partial section view of a second embodiment of the present invention.

1  Compressed air source
2  Flotation units
3  Main supply hose
4  Distribution valve REFERENCE NUMBERS -continued 5   Individual supply hoses
6   Inflatable bladder
7   Relief valve
8   Diffusing manifold
9   Bottom mesh/bottom cover
10  Top mesh/top cover
11  Buoyant growth medium
12  Air bubbles
13  Portion of air bubbles adhering to internal surfaces within flotation unit 2
14  Extension tube
15  Aquatic plants/live vegetation
16  Wind-powered compressor
17  Photoelectric-powered compressor
18  Photoelectric cell
19  Battery
20  Electric air pump
21  Controller
22  Wave-powered air pump
23  Waves
24  Elastic air chamber
25  Outlet tube
26  Outlet check valve
27  Inlet tube
28  Inlet check valve
29  Exhaust tube
30  Float valve
31  Ball float
32  Sealing face
33  Nesting unit
34  Solar-powered electric shocking system
35  Attraction/shocking pipe
36  Differential shocking electrode
37  Sharp spikes
38  Photoelectric cell
39  Storage battery
40  High-voltage converter and shock control unit
41  Bird perch
42  Bird-shocking electrodes
43  Upwardly sloping edge
44  Duckling jump location
45  Bottom of predator-resistant floating habitat
46  Sides of predator-resistant floating habitat
47  Top of predator-resistant floating habitat
48  Artificial plants
49  Lip on top of predator-resistant floating habitat
50  Internal filling material of predator-resistant floating habitat
51  Scrap pieces of polyester mesh
52  Scrap pieces of closed cell foam
53  Expandable foam
54  Predator-resistant sides of habitat
55  Nesting area
56  Brushy camouflage material
57  Bottom covering of habitat
58  Nesting cavity
59  Outer covering of habitat
60  Mold
61  Molded habitat body
62  Scrap pieces of nonwoven mesh material
63  Brush attachment wires
64  Molded habitat structure
65  Nesting waterfowl
66  Layers/sheets of nonwoven polyester mesh material

DETAILED DESCRIPTION OF INVENTION

The floating habitat of the present invention is designed to be renewably buoyant during its useful life, and it is also designed to be self-sustaining. The floating habitat is self-sustaining because it can withstand temperature extremes and also because its design minimizes the risk of damage by animals. In the preferred embodiment, buoyancy is maintained through the use of buoyant growth medium, inflatable bladders, and a self-compensating buoyancy system. Buoyancy can also be enhanced through the addition of gas-producing microorganisms. The floating habitat of the present invention can also be specialized to provide waterfowl nesting habitat.

The floating habitat of the present invention is equipped with components that supply pressurized air to the submerged portions of the structure in order to increase the overall buoyancy of the structure. There are several alternative configurations for the air supply system. The first embodiment of the self-pressurized floating habitat system is shown in top view in FIG. 1. A compressed air source 1 is shown mounted on top of flotation units 2. Although the drawing depicts the use of two flotation units 2, any number may be used, depending on the selected size of each flotation unit 2 and the required buoyancy and overall size of the floating habitat. Compressed air is produced by the compressed air source 1, pumped through the main supply hose 3 to the distribution valve 4, and then to the individual supply hoses 5.

FIG. 2 is a section view taken at section I-I of FIG. 1, and it shows the compressed air source 1, the flotation units 2, the main supply hose 3, the distribution valve 4, and an individual supply hose 5. FIG. 3 is a partial view of FIG. 2. It depicts one flotation unit 2 that is enlarged for magnification purposes. In FIG. 3, the major components comprising the flotation unit 2 are the individual supply hose 5, the inflatable bladder 6, the relief valve 7, the diffusing manifold 8, the bottom mesh 9, the top mesh 10, and buoyant growth medium 11. Compressed air from an individual supply hose 5 enters the inflatable bladder 6. The inflatable bladder 6 expands, and its internal air pressure increases until the pressure exceeds the opening pressure of the relief valve 7. When the relief valve 7 opens, excess air exits the inflatable bladder 6, passes through the relief valve 7, and is dispersed in the form of small air bubbles 12 through the diffusing manifold 8. A portion 13 of the air bubbles 12 adheres to either the bottom mesh 9, the top mesh 10, or the buoyant growth medium 11, thereby adding buoyancy to the structure. A portion of the bubbles 12 dissolves into the water that fills the void space between the nodules of growth medium 11, thereby increasing the dissolved air concentration of such water. A portion of the bubbles 12 is released through the openings of the bottom mesh 9 and top mesh 10 into the water surrounding the flotation unit 2, thereby increasing the dissolved air concentration in the water surrounding the flotation unit 2. The remainder of the bubbles 12 is released through the top mesh 10 into the atmosphere.

The purpose of the distribution valve 4 is to supply an equal portion of the compressed air to each flotation unit 2. This capability is particularly desirable in the event that one or more inflatable bladders 6 become punctured because it will allow the other bladders to continue to receive an adequate inflation supply.

The flotation units 2 may optionally be divided into multiple internal compartments with divider panels. The purpose of providing multiple internal compartments is to limit the loss of buoyant growth medium to one compartment in the event that the bottom mesh 9 or top mesh 10 is locally ruptured.

In FIG. 2, the flotation unit 2 is shown as a cylindrical shape. The flotation units may be alternately constructed with different shapes, such as oval or rectangular, in order to best suit certain applications for the structure. For any shape of configuration, the bottom mesh 9 and top mesh 10 may be comprised of separate materials, or, alternately, a single piece of material may be rolled so as to serve the function of both the bottom mesh 9 and top mesh 10. One purpose of the bottom mesh 9 and top mesh 10 is to contain the buoyant growth medium 11 while allowing the stems and roots of growing plants (not shown) to extend through the flotation unit into the surrounding water and atmosphere. One example of a suitable material for the bottom mesh 9 and top mesh 10 is polypropylene netting material with ¼-inch mesh opening size. The bottom mesh 9 and top mesh 10 may optionally be designed or modified to be resistant or unattractive to chewing animals, for example, by adding sand to the resin during the manufacturing process.

The buoyant growth medium 11 may be comprised of either natural material (e.g., wood chips) or synthetic material (e.g., shredded closed-cell polymer foam) that is compatible with the selected vegetation. Additional examples of natural materials that could be used for buoyant growth medium are: cork; balsa wood; pine wood; oak wood; and volcanic rock with naturally sealed air pockets. Additional examples of synthetic materials that could be used for buoyant growth medium are: perlite; polystyrene beads; polystyrene foam; vermiculite; perlite; hollow plastic balls (10 mm); solid polypropylene balls; polyethylene foam, closed cell; vinyl acetate foam, closed cell; polyurethane foam, closed cell; polyimide foam, closed cell; ionomer foam, closed cell; silicone foam, closed cell; PVC foam, closed cell; silicone sponge rubber, closed cell; neoprene sponge rubber, closed cell; natural gum sponge rubber, closed cell; and ECH sponge rubber, closed cell. The growth medium may optionally contain plant growth enhancers. Plant enhancers can include nutrients such as nitrogen, phosphorus, and potassium; pH modifiers; mineral supplements; and mycorrizha or other symbiotic soil-dwelling organisms.

The inflatable bladders 6 are constructed from a material that is airtight, durable and flexible over the expected range of environmental conditions. Examples of potentially suitable materials include polyvinyl chloride film, polyethylene film or pipe, polypropylene film, polyester film (such as MYLAR), butyl rubber, neoprene rubber, nitrile rubber, EPDM rubber, and silicone rubber. The material may optionally be transparent in order to discourage chewing damage by inquisitive animals such as muskrats and mink. The inflatable bladders can be used optionally to decrease the buoyancy of the structure by filling them with water. The water can be subsequently removed, if desired, by using the compressed air system.

A second embodiment of a flotation unit 2 is shown in cross section in FIG. 4. In this embodiment, an extension tube 14 is used to position the diffusing manifold 8 beneath the flotation unit 2. Excess air is released through the diffusing manifold 8 into the water body in which the structure is floating. The released air bubbles 12 rise through the water body, where a first portion of the bubbles 12 dissolves into the water, a second portion adheres to the roots of aquatic plants 15 that extend through the bottom mesh 9, and the remainder of the bubbles is dispersed as described for FIG. 3. An advantage of this "extended manifold" embodiment is that it provides a means for increasing the dissolved air concentration in the water body, especially in the vicinity of the structure.

Figure 5:
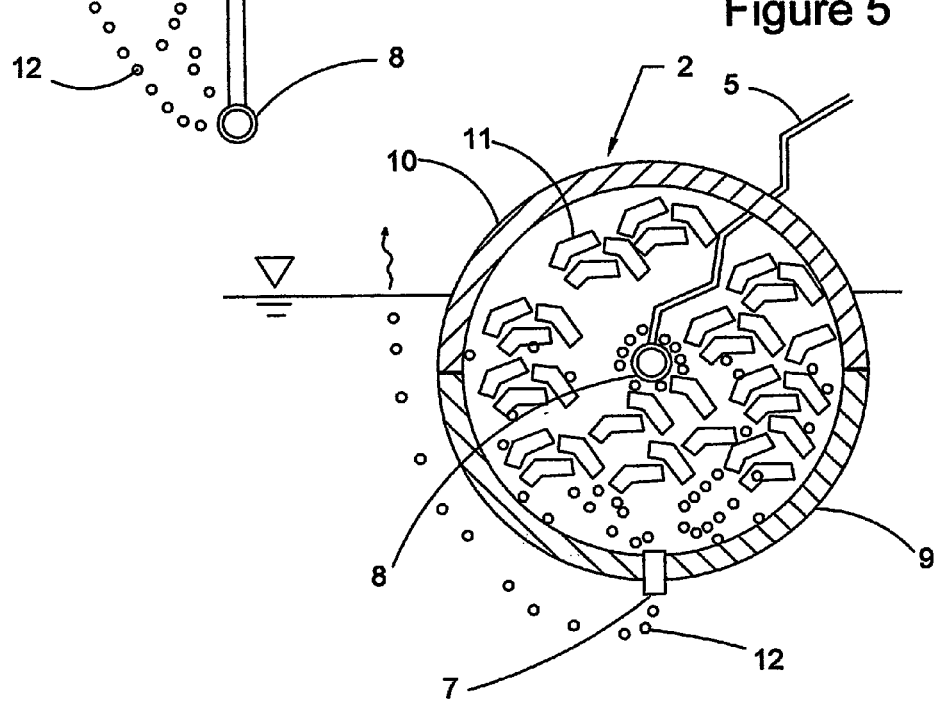
FIG. 5 is a section view of an alternative embodiment of the flotation unit of the present invention.

A third embodiment of a flotation unit 2 is shown in cross section in FIG. 5. In this embodiment, bottom cover 9 and top cover 10 are made of impermeable materials so that they cannot be penetrated by plants, air bubbles, or water. Air enters the flotation unit 2 through an individual supply hose 5 and is released through a diffusing manifold 8, causing the internal pressure of the flotation unit 2 to increase. When the pressure increases to the opening pressure of the relief valve 7, excess air is released through the relief valve 7 to the water body in the form of air bubbles 12. This embodiment may be advantageous for applications where plant growth on the structure is not desired.

Figure 6:
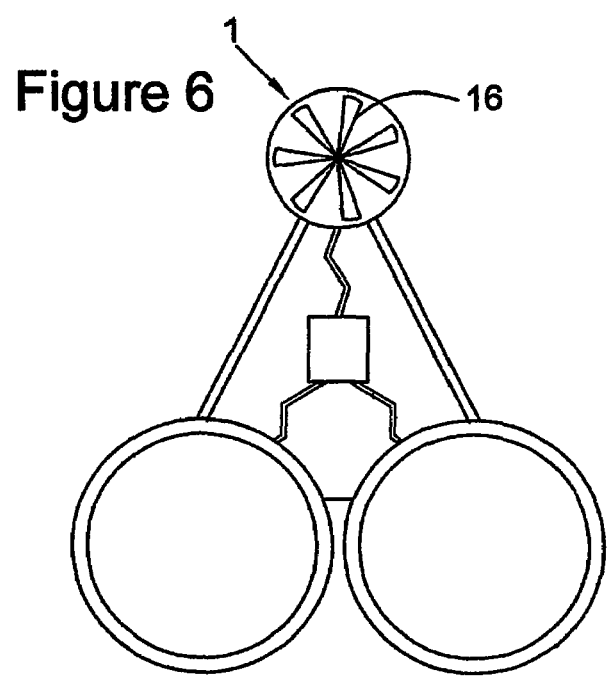
FIG. 6 is a side view of an alternative embodiment of the compressed air source.
Figure 7:
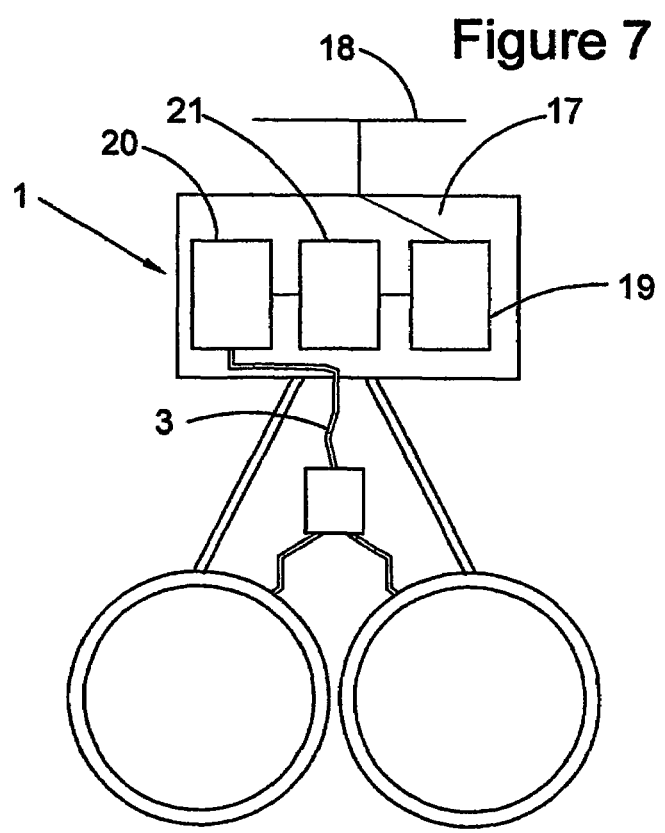
FIG. 7 is a side view of an alternative embodiment of the compressed air source.

Three alternative embodiments of the compressed air source 1 are shown in FIGS. 6, 7, 8 and 9. The first preferred embodiment of the compressed air source 1 shown in FIG. 6 is a wind-powered compressor 16. A second preferred embodiment of the compressed air source 1 is the photoelectric-compressor system 17 shown in schematic form in FIG. 7. Referring to FIG. 7, sunlight is converted to electrical current via a photoelectric cell 18. The electrical current is used to charge a battery 19, which is initially disconnected from the air pump 20. When the battery obtains a sufficient charge, as measured by the controller 21, the battery 19 is electrically connected to the air pump 20 by the controller 21, and the air pump 20 then supplies compressed air to the structure though a main supply hose 3 as described previously. When the electrical charge of the battery 19 falls below a preset level, as measured by the controller 21, the battery 19 is disconnected from the air pump 20 until the battery 19 has sufficiently recharged, at which time the pump cycle is repeated.

Figure 8:
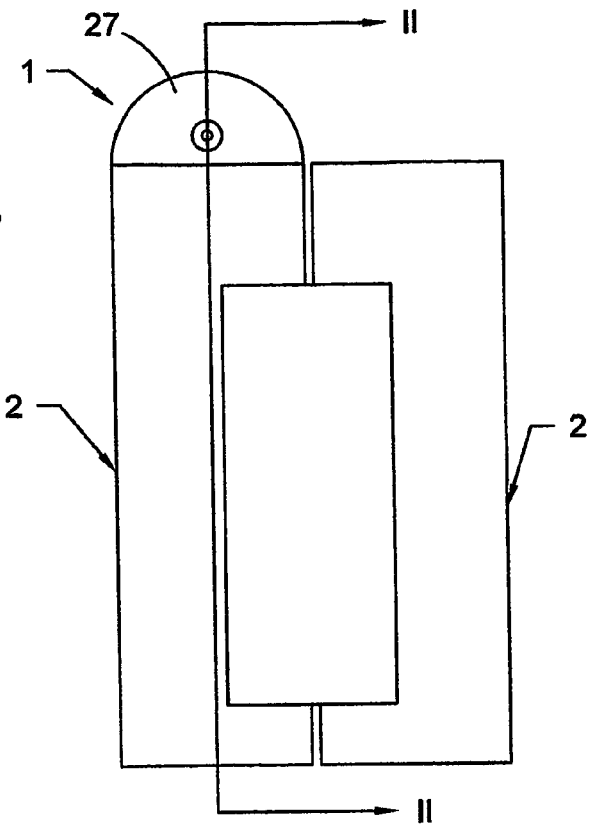
FIG. 8 is a top view of an alternative embodiment of the compressed air source of the present invention.
Figure 9:
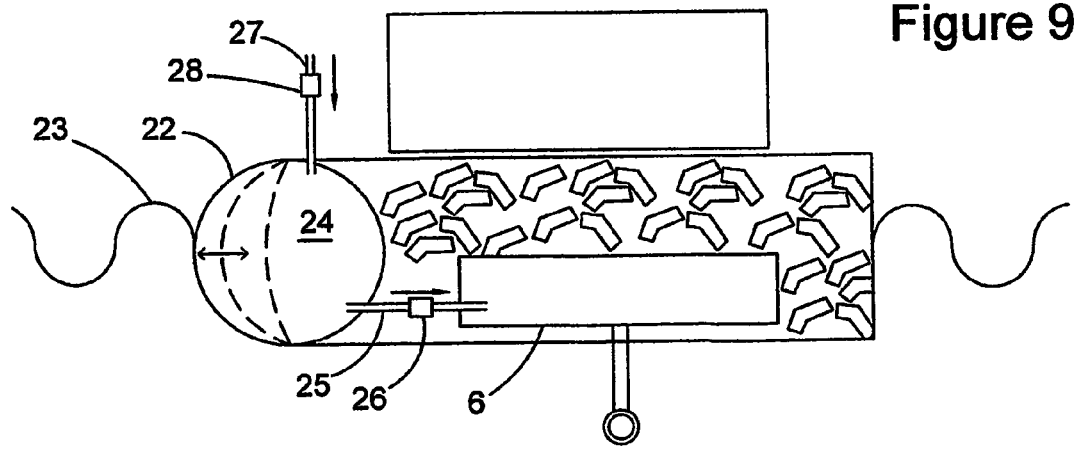
FIG. 9 is a section view taken at II-II of FIG. 8.

A third alternative embodiment of the compressed air source is shown in FIGS. 8 and 9. FIG. 8 is a plan view of the present invention with a wave-powered air pump 22. Also shown are two flotation units 2. FIG. 9 is a cross section view taken at section II-II of FIG. 8. A wave-powered air pump 22 is powered by waves 23 on the surface of the water body that are produced by wind or other action. The wave-powered air pump 22 is comprised of an elastic air chamber 24, an outlet tube 25, an outlet check valve 26, an inlet tube 27, and an inlet check valve 28. Waves 23 on the water surface cause the elastic air chamber 24 to alternately contract and expand, as shown by the dashed lines in FIG. 9. When the crest of a wave 23 pushes against the elastic air chamber 24, the elastic air chamber 24 contracts, and air is forced out of the elastic air chamber 24 through the outlet tube 25 and the outlet check valve 26 into the inflatable bladder 6. When the trough of a wave 23 contacts the elastic air chamber 24, the air chamber 24 expands, and air is sucked into the elastic air chamber 24 through the inlet tube 27 and the inlet check valve 28. The contraction-expansion cycle is repeated for each new wave 23, thereby forcing a pulse of air into the inflatable bladder 6 at each wave cycle. The purpose of the inlet check valve 28 and outlet check valve 26 is to permit air to flow through the wave-powered air pump 22 only in the direction shown by the arrows.

By sparging air bubbles under, around and through the floating habitat as described above, ice damage to the present invention is minimized. The presence of air bubbles under and around the floating habitat leads to thinner ice build-up around the habitat, and accordingly proportionately less ice damage to the present invention. In addition, plant growth is enhanced because the open water season around the floating habitat is extended by virtue of the reduction in ice mass.

Figure 10:
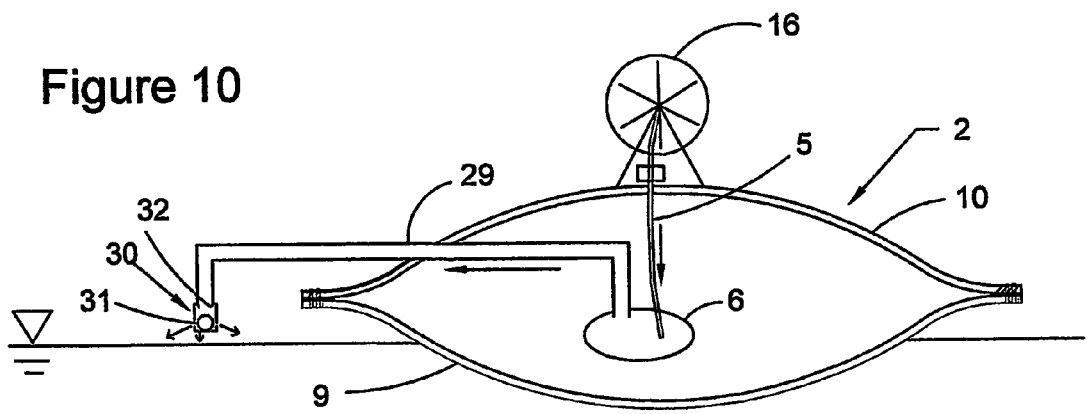
FIG. 10 is a partial illustration of the self-compensating system of the present invention.
Figure 11:
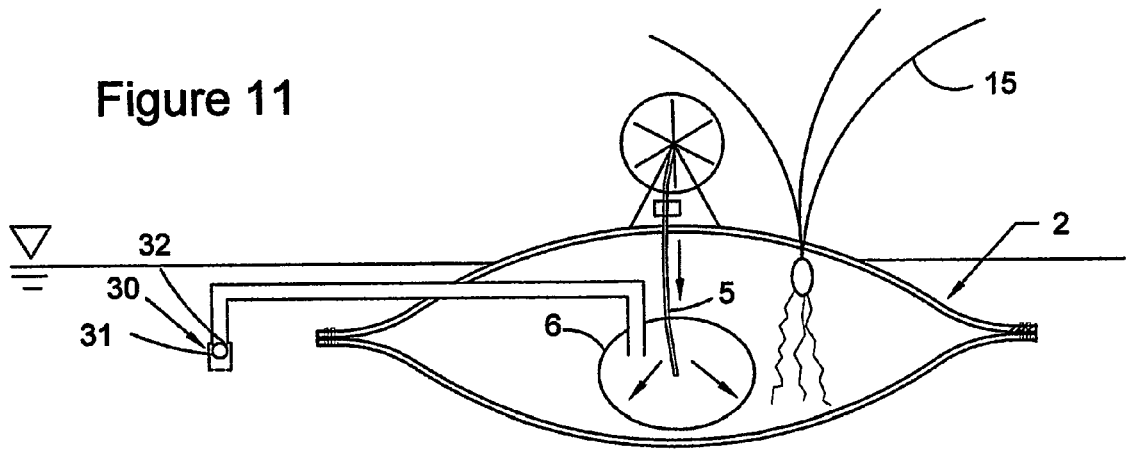
FIG. 11 is a partial illustration of the self-compensating system of the present invention.
Figure 12:
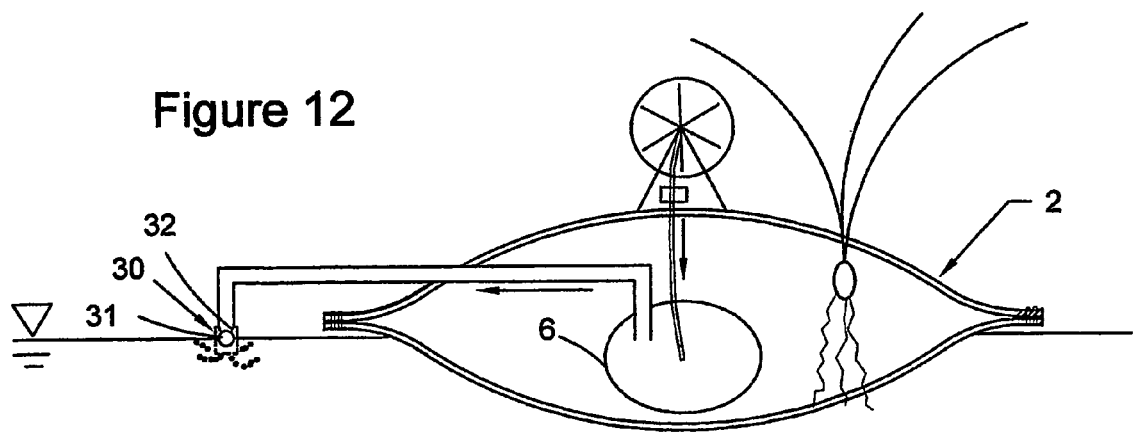
FIG. 12 is a partial illustration of the self-compensating system of the present invention.

The floating habitat structure can optionally be fitted with a self-compensating inflation device, or buoyancy system, that maintains the structure at a constant flotation level regardless of changes in the weight of objects placed on the structure. One embodiment of the self-compensating buoyancy system is shown in FIGS. 10, 11, and 12. In FIGS. 10, 11 and 12, the flotation units 2 are shown as being approximately oval in cross section, which is an alternative shape option for the flotation unit 2. Also in this configuration, separate pieces of material are used for the bottom mesh 9 and the top mesh 10, as shown in FIG. 10. The structure shown is comprised of a single flotation unit 2.

In FIG. 10, the structure has just been installed in a water body. A wind-powered compressor 16 is supplying compressed air through an individual supply hose 5 to an inflatable bladder 6. Air exits the inflatable bladder 6 via an exhaust tube 29, through the float valve 30, and is vented to the atmosphere around the ball float 31. Because the ball float 31 is in the lower, or non-floating, position, it does not seal against the sealing face 32 of the float valve 30, and air passes around the ball float 31 with no restriction in the exhaust end of the air pathway. Because excess air is vented to the atmosphere with no restriction in the exhaust end of the air pathway, there is no pressure buildup in the inflatable bladder 6, and, therefore, the bladder 6 is in an unexpanded condition.

In FIG. 11, the structure is shown after additional weight has been placed on it. In this example, the additional weight is shown as a growing aquatic plant 15. The weight of the plant 15 causes the structure to sink deeper into the water until the ball float 31 of the float valve 30 presses against the sealing face 32 of the float valve 30. When the ball float 31 seals against the sealing face 32, exhaust air is prevented from escaping into the atmosphere, and pressure rises in the inflatable bladder 6 as additional air enters through the individual supply hose 5. The increase in air pressure causes the inflatable bladder 6 to expand, as shown in FIG. 11. The expansion of the inflatable bladder 6 exerts a positive buoyant force on the structure.

In FIG. 12, the expansion of the inflatable bladder 6 has caused the structure to begin to rise in the water body. When the structure rises so that the ball float 31 is at the waterline, the air seal between the ball float 31 and the sealing face 32 is lost, and air begins to exit the inflatable bladder 6, which causes the inflatable bladder to contract and provide less buoyant force to the structure. An equilibrium level is established, as shown in FIG. 12, wherein the ball float 31 is lightly in contact with the sealing face 32, which causes the structure to achieve a steady-state level of flotation.

There are several alternative embodiments to the float valve system shown in FIGS. 10 through 12. For structures comprising a battery, such as the one shown in FIG. 7, a solid state pressure sensor can be mounted on the lower side of the structure. The sensor can be configured so as to read the differential pressure between the submerged depth and atmospheric pressure. When the structure settles deeper into the water, the measured differential pressure will increase. The sensor circuit can be designed to give an "on" signal, for example, when the differential pressure exceeds a preset limit. The circuit can be configured so as to close the exhaust valve when the structure settles too deeply into the water, thereby causing the structure to inflate and rise. Conversely, when the structure floats too high in the water, the circuit can cause the exhaust valve to open, which will cause the structure to deflate and undergo a decrease in buoyancy. This embodiment is referred to as the "submersible, differential pressure gauge system."

Another option for structures comprising a battery, such as that shown in FIG. 7, is a conductivity sensor that can be installed near the desired water level of the structure. If the structure settles too deeply into the water, the conductivity sensor will become submerged and give an "on" signal. This signal can be used to control the operation of the exhaust valve, as described above. This embodiment is referred to as the "conductivity switch."

For either electric or non-electric embodiments of the structure, the diffusing manifold 8 shown in FIG. 4 can be replaced by a restriction nozzle with a discharge point set near the desired waterline of the structure. The dimensions of the nozzle can be configured so that there is insignificant pressure drop through the nozzle when discharging to the atmosphere, but significant pressure drop when bubbling out into the water body. The operation of this embodiment would be similar to that described for the float valve system, except that there would be no mechanical seals required. This embodiment is referred to as the "exhaust nozzle."

As a buoyancy enhancement, gas-producing microorganisms can be added to the floating habitat. The floating habitat can be inoculated with these microorganisms by taking a sample of bacteria-rich soil and introducing it into the growth media. The soil is necessary to achieve inoculation but is not necessary to sustain the bacteria, which can be fed with a high-carbon substrate food source, such as molasses or sugar beet extract. The bacteria will survive the seasonal temperature fluctuations and will produce gases that are trapped in the floating habitat for some time until they escape through the surrounding mesh.

The floating habitat of the present invention can be specialized to provide a nesting structure for wild ducks and other waterfowl. Waterfowl nesting structures are beneficial for sustaining and increasing the production of wild waterfowl where natural nesting sites have been reduced by agriculture, drought, predation, or other causes.

Figure 13:
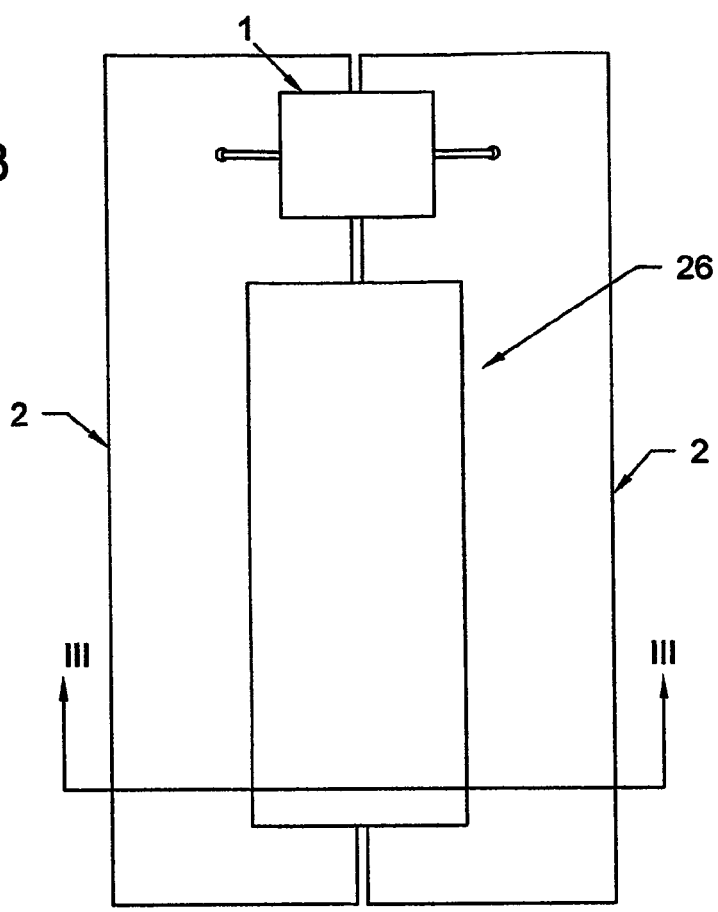
FIG. 13 is a top view of an embodiment of the present invention that is specialized for waterfowl nesting.
Figure 14:
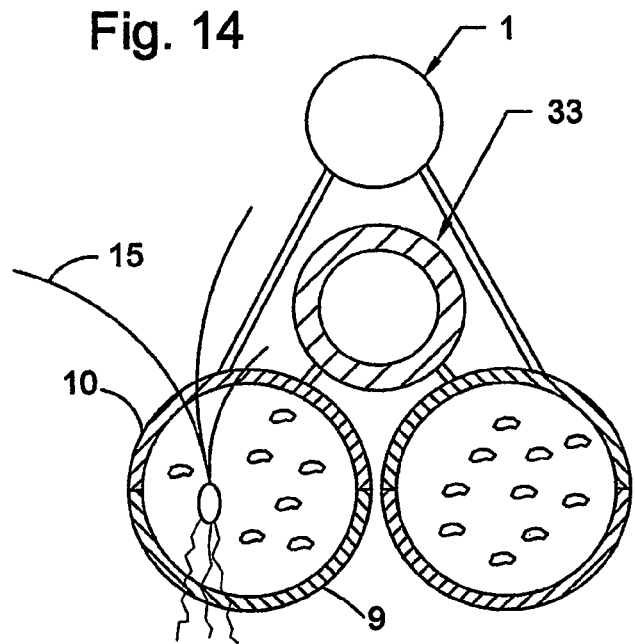
FIG. 14 is a section view taken at section III-III of FIG. 13.

FIG. 13 is a top view of a floating habitat structure that has been specialized for waterfowl nesting. FIG. 14 is a cross section view taken at section III-III of FIG. 13. The specialized waterfowl nesting structure shown in FIGS. 13 and 14 incorporates the flotation units 2, optional compressed air source 1, and additional components described below.

The nesting unit 33 is configured to be attractive to the particular species of waterfowl that is being encouraged to nest. One or more nesting units can be provided on any one floating habitat structure, either for the same or different species. In one preferred embodiment, commercially available HEN HOUSES may be installed on the structures to encourage nesting of, for example, mallard ducks. HEN HOUSES are wire-reinforced straw-filled tubes favored by mallard ducks. Another example of a nesting habitat is a gravel pad favored by plovers. Synthetic or natural grass plots are other examples of nesting habitat favored by other species of waterfowl. Where desired, the nest can be protected from swimming predators by raising the nesting unit 33 and/or installing a predator exclusion disk (not shown) or other predator control device.

Optional live vegetation 15 is selected based on the geographical location of the structure and the nesting preference of the species of waterfowl that is being encouraged to nest on the structure. For example, to attract mallards in northern states, bulrushes and cattails may be the preferred vegetation. At some locations, it may be preferable to omit live vegetation in order to prevent the structure from becoming rooted to the bottom of a shallow or dried-up pond. At other locations, it may be desirable to select the bottom mesh 9 so that plants can grow in the flotation units 2 but their roots cannot penetrate the lower side of the flotation unit 2.

In this embodiment, a compressed air source 1 is located on the structure so as to balance the structure properly, depending on the type of nesting unit 33 that is installed. The construction material and screen size of the top mesh 10 are selected to be attractive to the nesting waterfowl, to be safe for juvenile waterfowl, to provide a substrate for new vegetation growth, and to allow penetration of vegetation stems (when live vegetation is optionally planted within the flotation unit 2). An example of a potentially suitable material for the top mesh 10 is polymer-reinforced jute geotextile matting.

Optionally, two or more of the structures may be joined together so as to provide relatively sheltered water pockets between the individual structures. These sheltered pockets may provide a relatively safe habitat for juvenile waterfowl, and the increased area provided by multiple connected structures may encourage colony nesting of some desirable species or alternatively allow for a variety of waterfowl or shore bird species to enjoy suitable habitat on the same floating habitat system.

There are numerous advantages to the waterfowl habitat design of the present invention. First, the nesting structures can be located in relatively deep water far from shoreline, making them inaccessible to predators such as skunks and red fox. In addition, the structures may provide more nesting sites than could be provided by traditional post-mounted nesting stations, which require relatively shallow water locations. Second, the nest box portions of the structures can be adapted to match the nesting preference of a particular species of waterfowl. Third, the live vegetation on the structures can be selected to match the nesting preference of a particular species of waterfowl. Fourth, the structures are buoyant and will provide effective nesting habitat during periods of fluctuations of water level. Fifth, the floating habitat can optionally be equipped with a self-compensating buoyancy controller that allows the structure to automatically adapt to variations in weight. Lastly, the floating habitat structures are less expensive than the cost of installing a normal island in a pond and can be moved to new locations as desired.

Another embodiment of the present invention, not illustrated, is a closed bag system in which buoyant growth medium (or buoyant medium if plant growth is not an issue) is contained in a water-permeable or water-impermeable bag, and a waterfowl nesting structure is added to the floating habitat. The closed bag embodiments can include, optionally, any of the buoyancy mechanisms described above. If a water-impermeable bag were used, then the floating habitat could also include artificial turf or plants to achieve a visual effect similar to a floating habitat with naturally growing vegetation.

Figure 15:
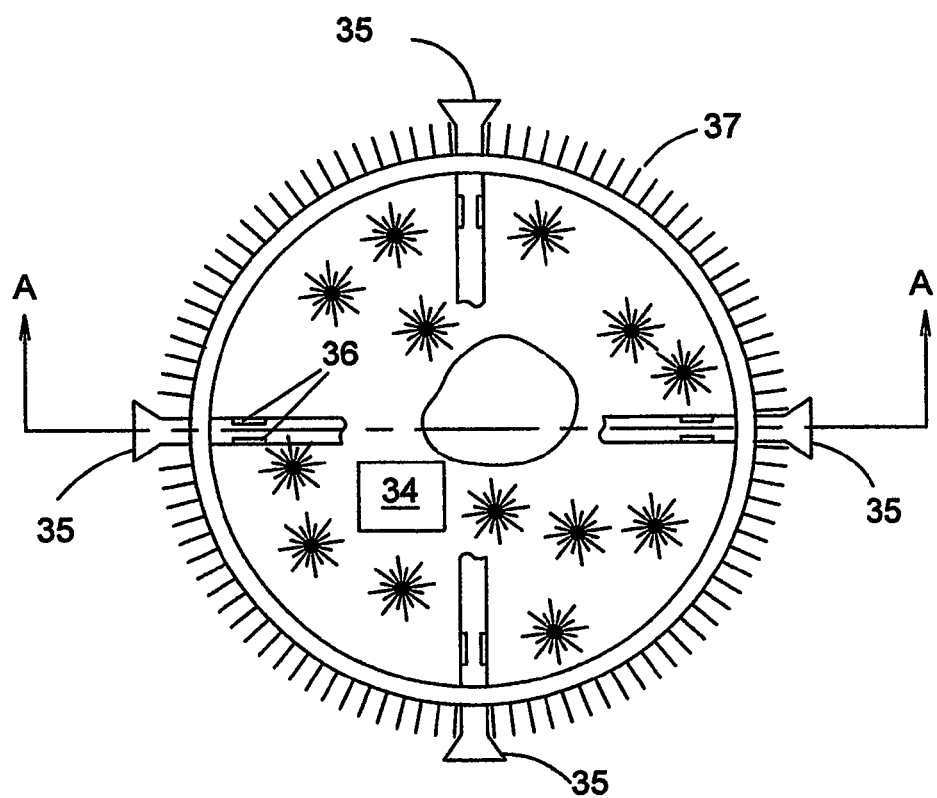
FIG. 15 is a top view of a habitat equipped with features for deterring mammalian predators.
Figure 16:
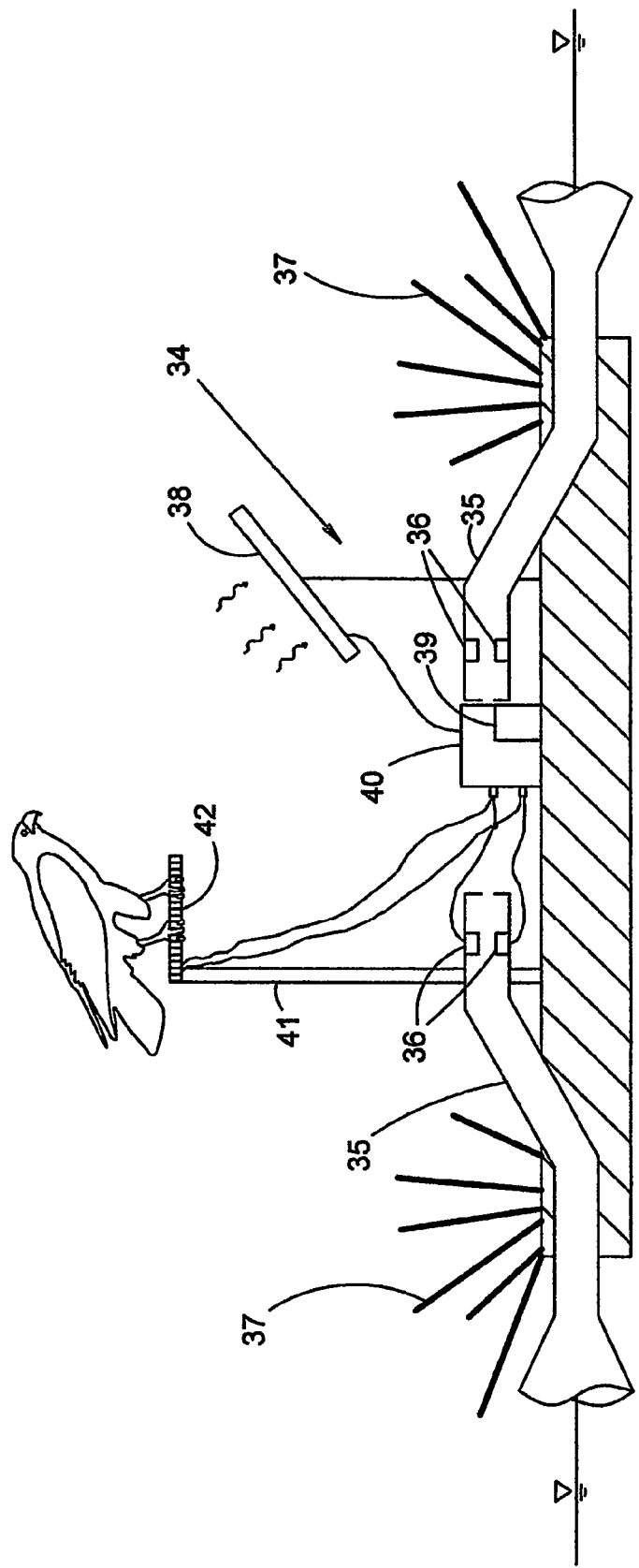
FIG. 16 is a section view of FIG. 15, with optional additional deterrent components for avian predators.

FIGS. 15 and 16 depict an embodiment of the present invention that includes additional predator-resistant features. The mammalian predator-resistant features of FIGS. 15 and 16 can optionally be accompanied by a predator call. In addition, a hen nesting decoy could be placed on the habitat as a means by which to attract the egg-robbing or duck-preying predators to the habitat.

Referring to FIG. 15, the mammalian predator-resistant features of this embodiment of the floating habitat are comprised of a solar-powered electric shocking system 34, attraction/shocking pipes 35, differential shocking electrodes 36, and sharp spikes 37. The spikes 37 can be buoyant or non-buoyant, depending upon the requirements of a particular situation, but they have to be rigid and sharp in order to perform their intended function. For example, the spikes could be made of plastic, metal, glass, or porcupine quills. The spikes could be made of the stainless steel "porcupine wire" sold by Nixalite of America Inc. or the stainless steel and polycarbonate BIRD-FLITE SPIKE manufactured by Bird Barrier America, Inc. The purpose of the predator-resistant features of the present invention is to provide aversion training to swimming mammalian predators, especially mink, which may be attracted to the floating habitat.

The mammalian predator-resistant features come into play when a mink (or similar predator) swims to the habitat and attempts to climb upon it. Due to the presence of sharp spikes 37 around the circumference of the habitat, and the fact that mink are naturally disposed to enter holes and tunnels, the animal is encouraged to enter an attraction/shocking pipe 35. As the animal travels through the pipe, it will eventually come into contact with differential shocking electrodes 36, which will provide a painful yet non-lethal electric shock to the animal. Over time, as the animal is exposed to repeated shocks, it will learn to avoid the floating habitat. The system can be modified as required to shock larger animals such as raccoons.

Referring to FIG. 16, the solar-powered electric shocking system 34 is comprised of a photoelectric cell 38, a storage battery 39, and a high-voltage converter and shock control unit 40. External components include the differential shocking electrodes 36, the attraction/shocking pipe 35, an optional bird perch 41, and optional bird-shocking electrodes 42. The optional bird-deterrent system works by providing a painful but non-lethal electric shock to the bird via differential bird-shocking electrodes 42 that are mounted on the perch 41. The shock control unit 40 may be comprised of a commercially available device designed to contain dogs or domestic fowl.

Figure 17:
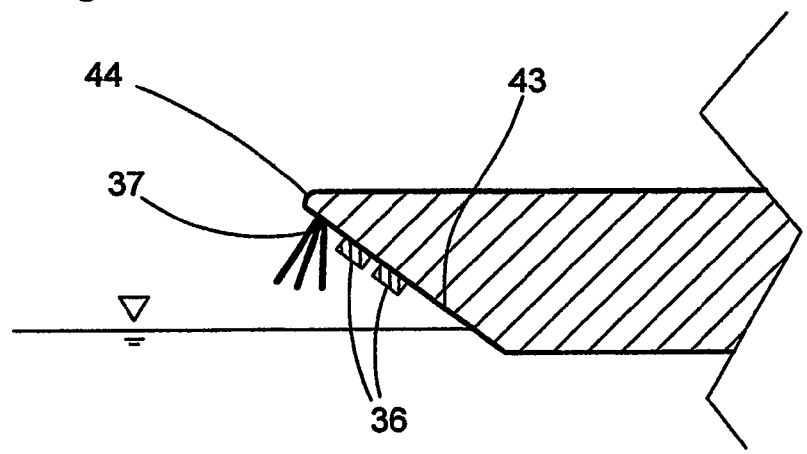
FIG. 17 is a partial section view of an alternate embodiment of the present invention that incorporates duckling jump location features.

FIG. 17 is a partial section view of an alternate embodiment of the present invention that is comprised of shocking electrodes 36, sharp spikes 37, an upwardly sloping edge 43, and one or more duckling jump locations 44. The features of this embodiment are designed to deter swimming predators, especially mink, from boarding the habitat. Differential shocking electrodes 36 may be separate components, as shown in FIG. 17, or they may be incorporated into the sharp spikes 37 when the spikes are made from an electrically conductive material. In this embodiment, the electrodes are situated above the waterline and the wave crest line so as to prevent electrical current from occurring in the water.

The upwardly sloping edge of the habitat 43 is designed to prevent swimming predators from obtaining a foothold on the habitat edge, except by grasping the shocking electrodes 36. The combination of these features will repel predators on their first attempt to board the habitat and will deter them from making additional attempts.

The duckling jump location 44 is designed to provide the newly hatched ducklings with a means of jumping off the habitat without contacting the shocking electrodes 36 or the sharp spikes 37. The ducklings will not need to return to the habitat, as ducklings typically do not return to their nest site after their initial departure.

Figure 18:
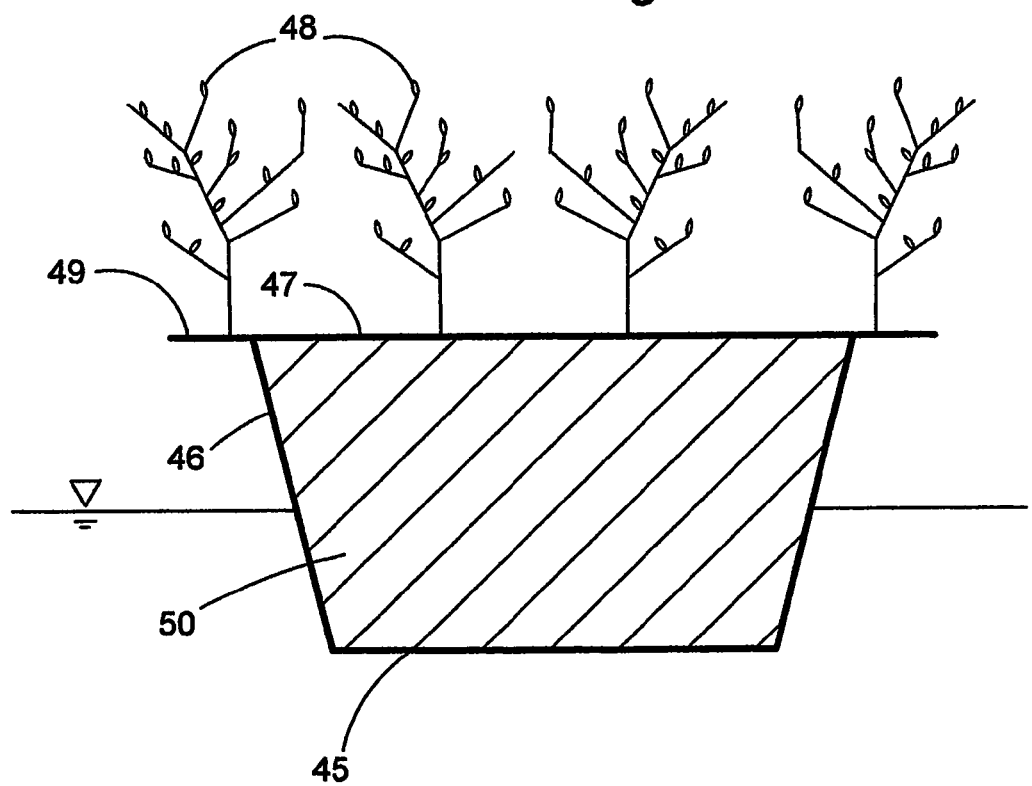
FIG. 18 shows another embodiment of a floating habitat that has been optimized for use as a predator-resistant habitat for nesting waterfowl.

FIG. 18 shows another embodiment of a floating habitat that has been optimized for use as a predator-resistant habitat for nesting waterfowl. The structure is comprised of a bottom 45, sides 46, top 47, and artificial plants 48. The bottom 45, sides 46, and top 46 are constructed of a lightweight and durable material such as high-density polyethylene sheets. The bottom 45 is particularly constructed so as to resist penetration by plant roots. The sides 46 are particularly constructed so as to resist climbing by swimming animals such as mink and raccoons. The sides 46 may be sloped outward as shown to make climbing more difficult. The top 47 is designed to be durable under year-round outdoor conditions and may optionally include a lip 49 around the perimeter to further resist boarding by swimming animals. The artificial plants 48 are constructed of thermoplastic or other suitable material designed to be durable under year-round outdoor conditions. In addition, the artificial plants 48 are constructed so as to be attractive to nesting waterfowl. Flotation for the structure is provided by the interior filling 50, which may be any suitable lightweight material, such as closed-cell foam or air. The floating height of the structure above the waterline is designed to be adequate so as to prevent swimming animals from jumping aboard.

In a preferred embodiment, the sides 46 of the structure are constructed of three flat sheets of material, resulting in a triangular habitat shape. In another embodiment, the sides are constructed of one or more curved sheets of material, resulting in a round or oval habitat shape. The structure can be made more natural in appearance by adding artificial boulders and logs, natural or artificial gravel, or natural straw to the top surface. When straw or other natural materials are used, they may be replenished seasonally, or as necessary.

In an alternative embodiment, the top 47 and interior 50 of the floating habitat are constructed so as to support the growth of natural plants, while the bottom 45 and sides 46 are constructed of materials that prevent penetration by growing plants. In this embodiment, the top 47 may be comprised of nonwoven mesh or geotextile material, while the bottom 45 is comprised of a material that is water-permeable but that resists penetration by plant roots. Examples of suitable bottom materials are woven and nonwoven landscaping fabrics, which are designed to resist plant penetration while allowing water to pass through. The sides 46 are constructed of the same materials as described in the previous embodiment.

In yet another alternative embodiment, the top 47, bottom 45 and interior 50 are designed to support the growth of natural plants, but the sides 46 are constructed of materials that prevent penetration by plants, thereby retaining the predator-resistance of the structure.

Several of the key materials that are used to manufacture the floating habitats may be available at very low cost in the form of scrap. These materials include polyester mesh, closed cell foam, and rigid plastic sheeting. The embodiments shown in FIGS. 19 and 20 utilize scrap materials to fabricate inexpensive, effective waterfowl nesting habitats.

Figure 19:
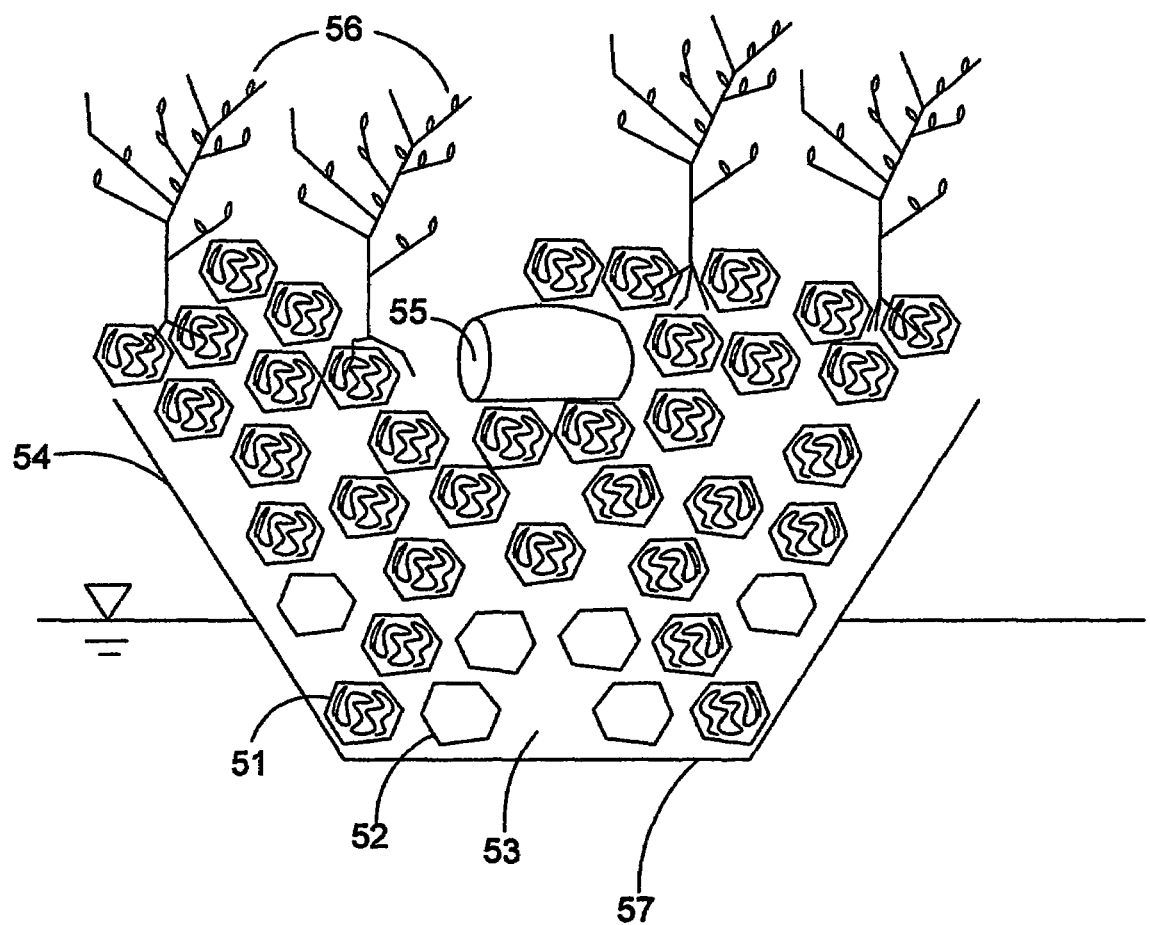
FIG. 19 is a schematic drawing of a floating habitat that utilizes scrap components and has predator-resistant sides and a camouflaged top.

FIG. 19 is a schematic drawing of a floating habitat that utilizes scrap components and has predator-resistant sides and a camouflaged top. This floating habitat is comprised of pieces of scrap polyester mesh 51 and optional scrap closed cell foam pieces 52, which are bound together by expandable foam 53. The expandable foam 53 is applied as a liquid. It penetrates into the pieces of polyester mesh 51 and also penetrates between the pieces of polyester mesh 51 and closed cell foam 52. When cured, the expandable foam 53 serves as an adhesive to hold the pieces together, and it also provides buoyancy to the structure.

The sides 54 are comprised of smooth, rigid plastic sheeting such as high-density polyethylene. The purpose of the sides 54 is to prevent swimming animals such as mink and raccoons from reaching the nesting area 55 located on the top of the structure. The nesting area 55 is surrounded by and hidden between pieces of scrap polyester mesh 51. Optional brushy camouflage material 56 may be attached to the top of the habitat to further aid in hiding the nesting area 55 from avian predators. The camouflage material 56 may be comprised of natural brush, artificial plants, or other suitable materials. Spikes or staples (not shown) may be used to attach the camouflage material 56 to the scrap pieces of mesh 51 within the habitat body.

The nesting area 55 may be shaped to be attractive to a particular species of nesting waterfowl; for example, it may be made in a tube-shaped form (as shown) to attract mallard ducks. Alternatively, it may be bowl-shaped or flat, in order to attract other species of waterfowl. Although only one nesting area 55 is shown in FIG. 19, the island may include more than one nesting area.

In a first alternative embodiment, the habitat is designed to allow plants to grow on the top surface of the habitat, and the plant roots are allowed to grow into the interior of the habitat body. The roots are prevented from protruding through the sides and bottom of the structure by predator-resistant sides 54 and bottom covering 57. The bottom covering 57 is comprised of a material that is permeable to water but does not allow penetration by roots. An example of a suitable material for the bottom covering 57 is plastic weed-prevention matting used for landscaping. This embodiment may be desirable at locations where the pond water level fluctuates enough so that the habitat may occasionally rest on the pond bottom, and any exposed roots might tend to attach the structure to the pond bottom.

In a second alternative embodiment, the bottom covering 57 is comprised of a material that allows plant roots to penetrate, such as nylon netting. This embodiment may be desirable for use in deep-water ponds, where the habitat is not likely to become attached to the pond bottom, and where the exposed plant roots would be beneficial as a food source for fish and waterfowl.

In a third alternative embodiment, plants are prevented from growing anywhere on or within the habitat by installing a bottom cover 57 that does not permit penetration by roots, and also installing a top cover (not shown) that does not allow penetration by plant stems. This embodiment may be desirable for use at locations where living plants would require excessive maintenance or otherwise create problems.

Figure 20:
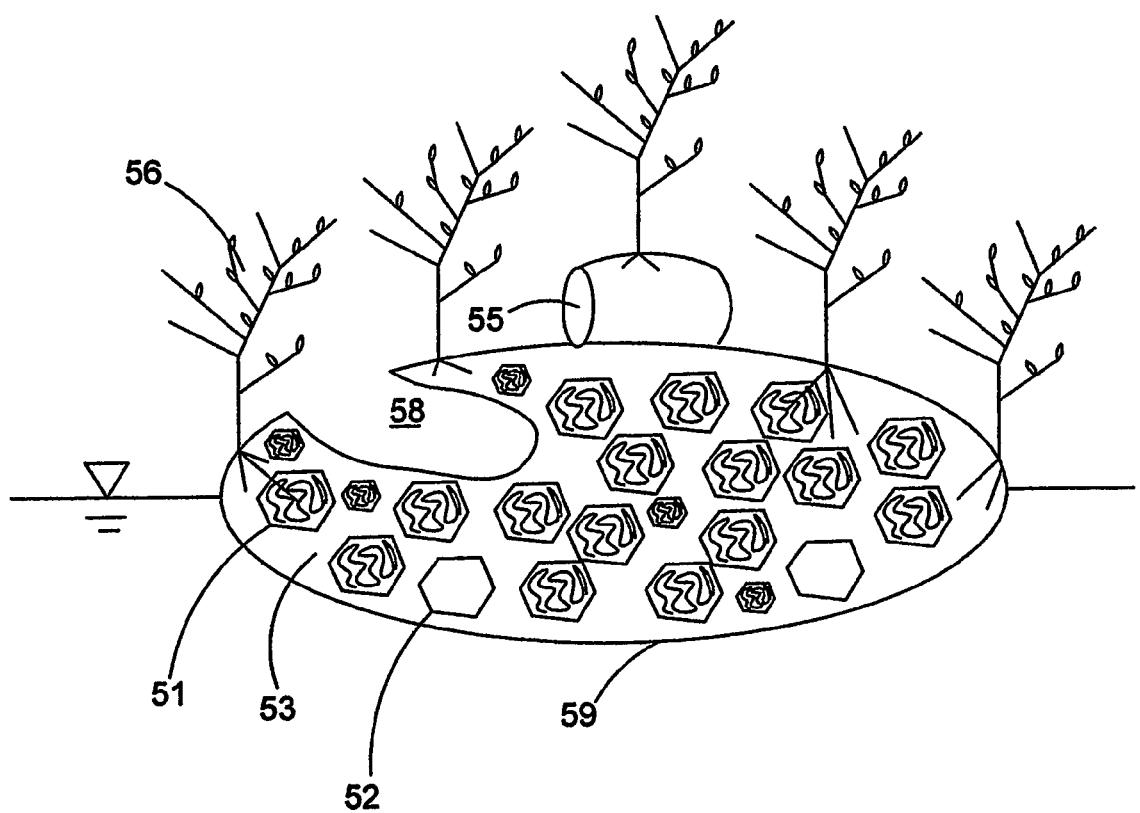
FIG. 20 is a schematic drawing of a floating habitat that utilizes scrap components and has a natural appearance and a camouflaged top.

The structure shown in FIG. 20 is designed to resemble a natural marsh object such as a muskrat lodge. It is comprised of scrap pieces of polyester mesh 51, optional scrap pieces of closed cell foam 52, and expandable foam 53. It also comprises a nesting area 55 and/or a nesting cavity 58, which are protected by a camouflage material 56. The top of the structure may optionally include a layer of jute or similar material (not shown), which may improve the natural appearance of the structure and promote plant growth.

In a first alternative embodiment, the outer covering 59 is comprised of a durable, water-permeable material, such as woven nylon. In a second alternative embodiment, the outer covering 59 is formed by melting and fusing the outer fibers of the pieces of polyester mesh 51 and closed cell foam 52.

The embodiments shown in FIG. 20 may be preferable to the more predator-resistant embodiment shown in FIG. 19 at locations where visual aesthetics and/or cost are important and swimming predators are not a major problem.

Figure 21:
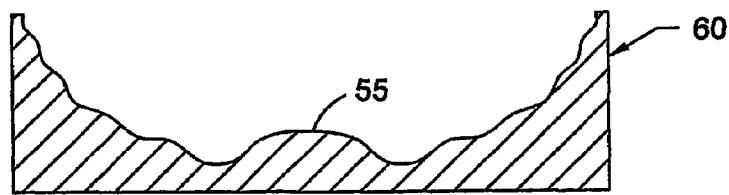
FIG. 21 is a schematic drawing of a mold used to fabricate a molded habitat made from scrap materials.

FIGS. 21-24 illustrate another embodiment of a floating habitat that is optimized for waterfowl nesting and low-cost construction. As shown in FIG. 21, the habitat body (not shown) is formed upside down in a mold 60. The mold 60 is generally saucer-shaped, with natural freeform contours and a nesting area 55 incorporated into the shape.

Figure 22:
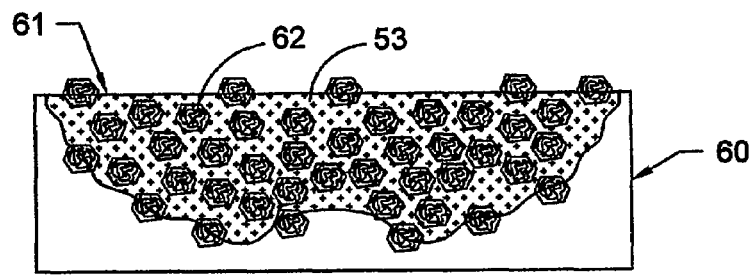
FIG. 22 is a schematic drawing of the first step of constructing a molded habitat made from scrap materials.

As shown in FIG. 22, the molded habitat body 61 is formed by laying scrap pieces of nonwoven mesh material 62 into the mold 60. The mesh material 62 may optionally be comprised of scrap pieces from other manufacturing processes. Expandable foam 53 is sprayed into and between the pieces of mesh 62, forming a buoyant, rigid structure.

Figure 23:
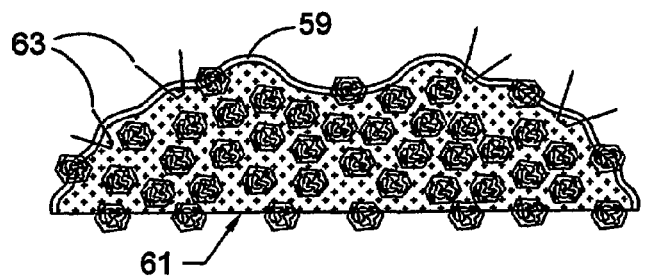
FIG. 23 is a schematic drawing of the second step of constructing a molded habitat made from scrap materials.

FIG. 23 shows the molded habitat body 61 after it has been removed from the mold (not shown) and placed in an upright position. An optional outer covering 59 made from burlap or similar material (or, alternately, a natural-looking synthetic material) may be attached to the habitat body 61 with a suitable adhesive. Brush attachment wires 63 are inserted into the habitat body 61.

Figure 24:
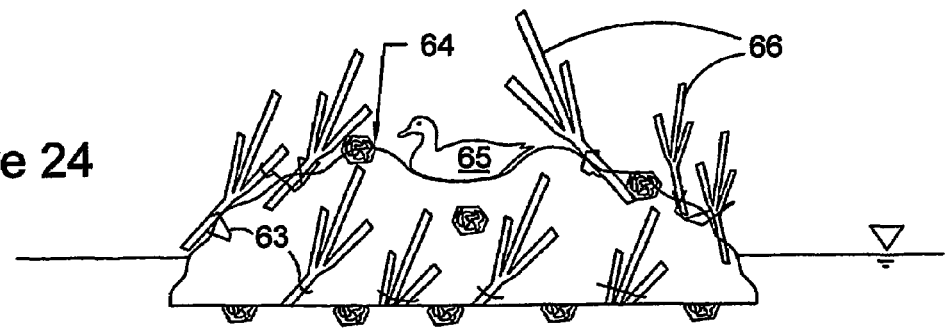
FIG. 24 is a schematic drawing of the third step of constructing a molded habitat from scrap materials.

FIG. 24 shows the molded habitat structure 64 in use by a nesting waterfowl 65. Pieces of natural brush 66 are attached to the surface of the habitat structure 64 by means of the brush attachment wires 63. The brush 66 provides protective camouflage cover to nesting waterfowl 65 and also renders the structure more natural-looking for aesthetic purposes.

By selecting the type of outer covering 59 and the amount of expandable foam 53, the habitat can be optionally made so as to either promote or prevent the establishment of aquatic plants. In general, most fabrics made from natural materials, or from coarsely woven synthetic materials, are penetrable by plant roots and stems. Materials made from finely woven synthetics (such as weed-proof landscaping fabric) are not penetrable by plants and, therefore, inhibit establishment of plants on the habitat structures. Plant roots and stems are easily able to penetrate the pieces of nonwoven mesh, but they are not able to easily penetrate pieces of closed cell foam or expandable foam; therefore, increasing the percentage of closed cell foam or expandable foam will have the effect of retarding plant growth within the habitat structure.

Figure 25:
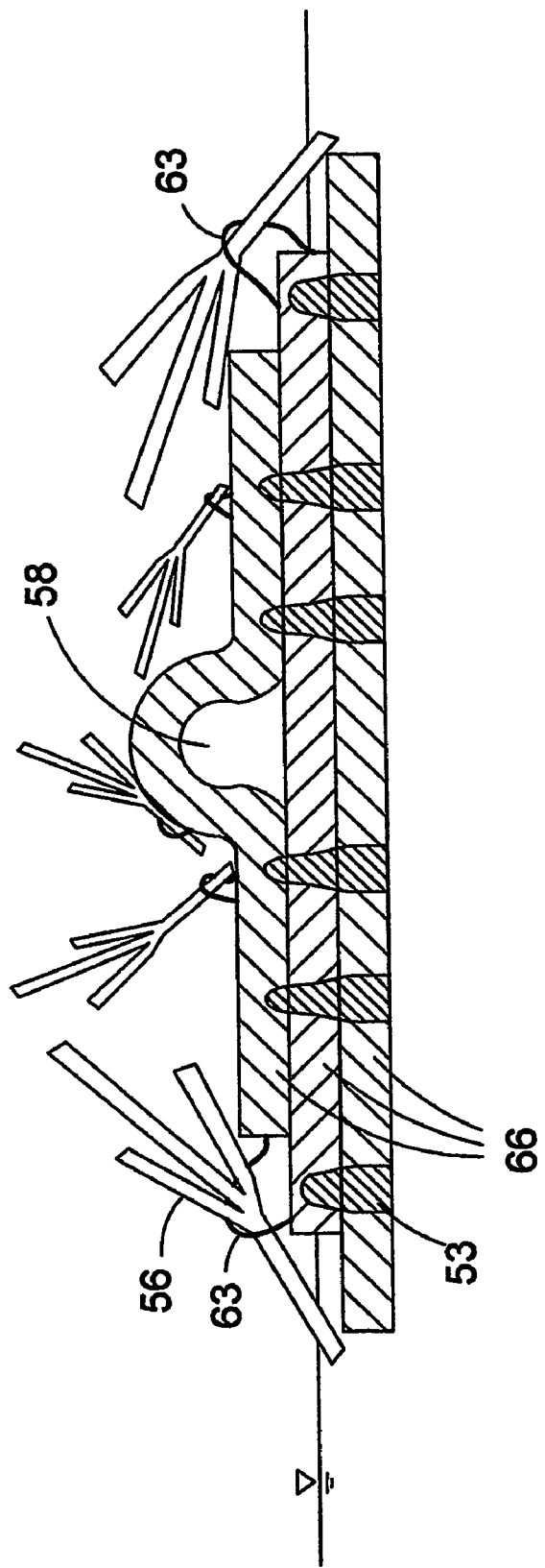
FIG. 25 is a section view of a floating habitat that is comprised of nonwoven polyester mesh sheets, expanding foam sealant, and one or more nesting cavities.

FIG. 25 illustrates yet another embodiment of the present invention. This embodiment is a floating habitat comprised of one or more layers or sheets of nonwoven polyester mesh material 66, expanding foam sealant 53, and brushy camouflage material 56. A nesting cavity 58 is shown as an arch in the top layer of nonwoven polyester mesh material 66; alternately, the nesting cavity 58 could be made as a separate unit (not shown) and attached to the top of the floating habitat. Multiple nesting units could be installed on the floating habitat if desired. Brushy camouflage material 56 is attached to the nonwoven polyester mesh material 66 by attachment wires 63 or any similar conventional means of attachment. Expanding foam sealant 53 provides buoyancy to the structure and also bonds the layers of nonwoven polyester mesh material together.

An optional feature for any of the embodiments described above is an anchor tether with swivel capability that provides flexibility so as not to impair the optimal buoyancy of the floating habitat.

Although several embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

REFERENCES

Mark W. Clark, "Biophysical Characterization of Floating Wetlands (Flotant) and Vegetative Succession of a Warm-Temperate Aquatic Ecosystem," Univ. of Florida Graduate School Dissertation (2000).

Edward H. Hogg and Ross W. Wein, "Typha Mat Buoyancy," Ecology, Vol. 69, No. 4 (August 1988).

Definitions

The term "ECH" means epichlorohydrin.
The term "EDPM" means ethylene-propylene-diene-methylene.
The term "PVC" means polyvinyl chloride.
The term "waterfowl" means a bird that frequents water and is not intended to be limited to swimming game birds.

We claim:

1. A floating habitat comprising one or more flotation units and a source of compressed air,
   wherein each flotation unit comprises an inflatable bladder having a relief valve and a diffusing manifold attached thereto, a bottom mesh, a top mesh, and a buoyant growth medium;
   wherein the bottom mesh and the top mesh form an enclosure housing;
   wherein the inflatable bladder, the relief valve, the diffusing manifold, and the buoyant growth medium are contained inside the enclosure housing;
   wherein the inflatable bladder has an internal air pressure, and the relief valve has an opening pressure;

wherein compressed air from the source of compressed air enters the inflatable bladder until the internal air pressure of the inflatable bladder exceeds the opening pressure of the relief valve, thereby causing the relief valve to open;

wherein when the relief valve opens, excess air exits the inflatable bladder, passes through the relief valve, and is dispersed in the form of small air bubbles through the diffusing manifold; and wherein a portion of the air bubbles adheres to the bottom mesh, the top mesh, or the buoyant growth medium, or a combination of the bottom mesh, the top mesh, and the buoyant growth medium, thereby adding buoyancy to the floating habitat.

2. A floating habitat comprising one or more flotation units and a source of compressed air, wherein each flotation unit comprises an inflatable bladder having a relief valve, an extension tube and a diffusing manifold attached thereto, a bottom mesh, a top mesh, and a buoyant growth medium;

wherein the bottom mesh and the top mesh form an enclosure housing;

wherein the inflatable bladder and the buoyant growth medium are contained inside the enclosure housing;

wherein the extension tube positions the diffusing manifold outside the enclosure housing;

wherein the inflatable bladder has an internal air pressure, and the relief valve has an opening pressure;

wherein compressed air from the source of compressed air enters the inflatable bladder until the internal air pressure of the inflatable bladder exceeds the opening pressure of the relief valve, thereby causing the relief valve to open;

wherein when the relief valve opens, excess air exits the inflatable bladder, passes through the relief valve, and is dispersed in the form of small air bubbles through the diffusing manifold;

wherein a portion of the air bubbles adheres to the bottom mesh, the top mesh, or the buoyant growth medium, or a combination of the bottom mesh, the top mesh, and the buoyant growth medium, thereby adding buoyancy to the floating habitat;

wherein the floating habitat is situated on a body of water; and wherein excess air is released through the diffusing manifold into the body of water in the form of air bubbles.

3. The floating habitat of claim 1 or 2, wherein the air bubbles that are released from the diffusing manifold are sparged under, around or through the floating habitat, thereby minimizing ice damage to the floating habitat and enhancing plant growth.

4. The floating habitat of claim 1 or 2, wherein the buoyant growth medium comprises further natural material.

5. The floating habitat of claim 1 or 2, wherein the buoyant growth medium further comprises one or more plant growth enhancer(s).

* * * * *